United States Patent [19]

Yannas et al.

[11] 4,350,629

[45] Sep. 21, 1982

[54] PROCEDURES FOR PREPARING COMPOSITE MATERIALS FROM COLLAGEN AND GLYCOSAMINOGLYCAN

[75] Inventors: Ioannis V. Yannas, Newton Center, Mass.; Martin J. Forbes, Kirkland, Canada

[73] Assignee: Massachusetts Institute of Technology, Cambridge, Mass.

[21] Appl. No.: 287,998

[22] Filed: Jul. 29, 1981

[51] Int. Cl.³ .................... C07G 7/00; C08H 1/00; C08H 1/06
[52] U.S. Cl. .................... 260/123.7; 106/155; 106/157; 128/335.5; 128/349 R; 128/DIG. 8
[58] Field of Search ............. 260/123.7; 106/155, 106/157

[56] References Cited

U.S. PATENT DOCUMENTS

| | | | |
|---|---|---|---|
| 3,527,225 | 9/1970 | Smith | 260/123.7 UX |
| 4,060,081 | 11/1977 | Yannas et al. | 128/156 |
| 4,233,360 | 11/1980 | Luck et al. | 260/123.7 X |
| 4,280,954 | 7/1981 | Yannas et al. | 260/123.7 |

*Primary Examiner*—Howard E. Schain
*Attorney, Agent, or Firm*—Arthur A. Smith, Jr.; David E. Brook

[57] ABSTRACT

This invention relates to crosslinked collagen and glycosaminoglycan materials, and to procedures for preparing such materials. It has been discovered that if collagen fibrils in an aqueous acidic solution are contacted with a crosslinking agent before being contacted with glycosaminoglycan, the materials produced have extremely low levels of thrombogenicity. Such materials are well suited for in-dwelling catheters, blood vessel grafts, and other devices that are in continuous contact with blood for long periods of time.

6 Claims, No Drawings

PROCEDURES FOR PREPARING COMPOSITE MATERIALS FROM COLLAGEN AND GLYCOSAMINOGLYCAN

DESCRIPTION

GOVERNMENT SUPPORT

The invention described herein was supported in whole or in part by a grant from the National Institutes of Health.

TECHNICAL FIELD

This invention is in the fields of polymeric materials and biocompatible materials.

BACKGROUND ART

Composite materials made of collagen and glycosaminoglycan (GAG) have been shown to be highly useful for certain biochemical applications. For example, U.S. Pat. No. 4,060,081 (Yannas et al, 1977), the teachings of which are hereby incorporated by reference, discloses a multilayer membrane suitable for use as synthetic skin. The bottom layer, which is placed in contact with a woundbed, is a highly porous lattice comprising collagen that is crosslinked with GAG. This lattice provides a biophysical supporting structure in which cells can migrate and proliferate to heal the wound.

The typical procedures that have been used in the past to prepare collagen/GAG composite materials are described in U.S. application Ser. No. 30,183, filed on Apr. 16, 1979, now U.S. Pat. No. 4,280,954 and U.S. application Ser. No. 169,897, filed on July 17, 1980, now abandoned; the teachings of both of those applications are hereby incorporated by reference. Briefly, a preferred embodiment of those procedures comprises the following steps, in sequence:

1. Mechanically cutting and grinding a source of collagen into particulate form.
2. Soaking the particulate collagen in dilute acetic acid.
3. Homogenizing the solution in a blender.
4. Adding a source of glycosaminoglycan which has been ground into particulate form. Typically, enough GAG is added to the solution to comprise about 6% to about 12% by dry weight of the composite material. The collagen/GAG mixture normally precipitates out of the acidic solution and forms a fibrous dispersion.
5. The precipitate is homogenized in a blender.
6. The solution is contacted with a crosslinking agent such as glutaraldehyde.
7. The solution is quickly frozen in a shallow pan.
8. The frozen dispersion is subjected to a high degree of vacuum, causing the acidic fluid to evaporate while the spatial configuration of the partially crosslinked fibrils is maintained.

The composite material thus formed may be treated by additional procedures to remove all traces of glutaraldehyde and to increase the crosslinking density and strength of the composite material.

The resulting collagen/GAG composite material exhibits some degree of incompatibility with the blood. For example, a small amount of platelet aggregation may occur over a period of several months if blood is in continuous contact with this material. This degree of blood incompatibility might be tolerable if the collagen/GAG composite material is to be biodegraded over a relatively short period of time, as is the case when it is used as artificial skin. However, that level of blood incompatibility can lead to certain problems in the use of collagen/GAG composite materials for prosthetic devices which are not rapidly biodegraded and which are in continuous contact with blood. For example, collagen/GAG material, in a less porous form than the lattice used for synthetic skin, may be useful for in-dwelling catheters, blood vessel replacement material, and other prosthetic devices. For such uses, it is advantageous to utilize a composite material that does not cause platelet aggregation to any detectable extent.

DISCLOSURE OF THE INVENTION

This invention relates to a method of creating collagen and glycosaminoglycan (GAG) composite materials that have extremely high levels of blood compatibility. The Applicants have discovered that if an aqueous dispersion of collagen which has been swollen in acid is contacted with a crosslinking agent such as glutaraldehyde prior to adding GAG to the solution, the resulting composite material will cause extremely low or undetectable levels of blood platelet aggregation. The invention described herein also relates to composite materials formed by this method. These materials are highly useful for prosthetic devices that will remain in contact with blood for very long periods of time, including indwelling catheters, blood vessel grafts, and other prosthetic devices that are not rapidly biodegraded.

BEST MODE FOR CARRYING OUT THIS INVENTION

In one preferred embodiment of this invention, a source of collagen is ground into particulate form and contacted with dilute acetic acid. The acidic solution is stirred to ensure thorough contact of all collagen with acid. The collagen is subsequently allowed to swell for 72 hours to remove all native banding.

After swelling, a crosslinking agent comprising glutaraldehyde is added in the form of an aqueous solution. The final glutaraldehyde concentration is approximately equal to 0.5% weight/volume. The solution normally is stirred while the glutaraldehyde is being added.

Following the addition of glutaraldehyde, a solution of chondroitin 6-sulfate (which is a glycosaminoglycan) is added to the acidic collagen solution. The chondroitin 6-sulfate is first dissolved in dilute acetic acid, and added dropwise to the collagen solution while it is being stirred.

The resulting dispersion may be treated in any of several ways. In order to create a prosthetic device, it may be frozen and lyophilized. In order to test its blood compatibility properties, it may be filtered, air-dried, ground into particulate form, and dispersed in physiological saline solution.

EXAMPLES

Example 1: Preparation of Collagen/GAG Material

Collagen from bovine hide, prepared by the methods described by M. Komanowsky et al, *J. Amer. Leather Chemists Assn.* 69: No. 9, p. 410–422 (1974), was donated by H. I. Sinnamon of the U.S. Dept. of Agriculture. 0.55 g. of freeze-dried collagen was ground in a Wiley mill (A. H. Thomas Co., Phila. PA) to a 60 mesh particle size. It was added to 200 ml of 0.05 M aqueous acetic acid. This solution was stirred for 60 minutes in an ice-jacketed blender (Eberbach Corp., Ann Arbor, MI) on a 2-speed power unit (Waring Co., Hartford, CT) set on high speed with the line voltage reduced to 50% of 120 volts. Following this blending step, the solution was placed in a tightly closed glass jar and the collagen was allowed to swell for 72 hours at 4° C.

A solution of 25% glutaraldehyde ("Baker-analyzed" reagent grade, J. T. Baker Co., Phila. PA) in distilled water was prepared. A sufficient quantity of this solution was added to the acidic collagen solution to comprise 0.5% glutaraldehyde volume per volume. The glutaraldehyde solution was added while the dispersion was blended for one hour in an overhead blender (Hamilton Beach Div. of Scovill, Washington, N.C.) set on the low speed with the line voltage reduced to 60% of 120 volts.

0.0578 g chondroitin 6-sulfate was dissolved in 10 ml of 0.05 M acetic acid. This solution was added to 175 ml of the glutaraldehyde-treated collagen dispersion. The addition was performed over a period of 5 minutes while the dispersion was being blended in the overhead blender.

Shortly thereafter, the dispersion was filtered in a Buechner funnel. This filtering step was completed in about 20 minutes. The resulting wet membrane was then air-dried and milled to a 60 mesh particle size. It was dispersed in physiological saline solution (0.15 M NaCl, pH7) prior to being contacted with blood platelets.

Example 2: Preparation of Collagen/GAG Control Materials

Two other dispersions of collagen/GAG were prepared as described above, with the following changes. In one specimen, the glutaraldehyde crosslinking step was omitted. In the other specimen, chondroitin 6-sulfate was added to the collagen dispersion prior to the addition of glutaraldehyde.

Example 3: Blood Compatibility Testing

Blood plasma that was rich in platelet content was obtained from healthy, drug-free human donors (Beth Israel Hospital, Boston, MA) by using the procedures described in F. H. Silver et al, "Glycosaminoglycan Inhibition of Collagen-Induced Platelet Aggregation," *Thrombosis Research* 13: 267–277 (1978). Platelet clotting was measured with an aggregometer (Chrono-Log Corporation Model 300, Broomall, PA).

When platelet-rich plasma was contacted with the collagen/GAG dispersion that had not been contacted with glutaraldehyde, the collagen/GAG material caused rapid formation of a platelet clot. When the platelet-rich plasma was contacted with the collagen/GAG that had been contacted with glutaraldehyde subsequent to the addition of chondroitin 6-sulfate, a small amount of platelet aggregation occurred if the dispersion had been stored for a period of several months in physiological saline prior to being contacted with platelet-rich plasma. By contrast, when the glutaraldehyde crosslinking step preceded the addition of chondroitin 6-sulfate, as described in Example 1, no platelet aggregation could be detected, regardless of whether the dispersion was stored in physiological saline for up to one month prior to being contacted with platelet-rich plasma.

INDUSTRIAL APPLICABILITY

This invention has industrial applicability in the preparation of collagen prosthetic devices that have very high levels of blood compatibility.

EQUIVALENTS

Those skilled in the art will recognize, or be able to ascertain using no more than routine experimentation, numerous equivalents to the specific procedures described herein. Such equivalents are considered to be within the scope of this invention, and are covered by the following claims.

We claim:

1. A method for preparing a crosslinked collagen-glycosaminoglycan composite material, comprising:
   a. soaking collagen in an aqueous acidic solution having a pH of below about six;
   b. contacting said solution with a crosslinking agent; and
   c. contacting a source of glycosaminoglycan with said solution.

2. In the method of preparing crosslinked collagen-glycosaminoglycan composite material, the improvement of contacting collagen, which has been soaked in an aqueous acidic solution, with a crosslinking agent prior to contacting said collagen and said crosslinking agent with glycosaminoglycan.

3. A method of claims 1 or 2 wherein said aqueous acidic solution comprises acetic acid.

4. A method of claims 1 or 2 wherein said crosslinking agent comprises glutaraldehyde.

5. A method of claims 1 or 2 wherein said glycosaminoglycan is selected from the following group: chondroitin 6-sulfate, chondroitin 4-sulfate, heparin, heparin sulfate, keratan sulfate, dermatan sulfate, or chitin.

6. A crosslinked collagen-glycosaminoglycan composite material made by the methods of claims 1 or 2.

* * * * *